(12) United States Patent
Kaji et al.

(10) Patent No.: US 7,850,844 B2
(45) Date of Patent: Dec. 14, 2010

(54) LIQUID DELIVERY DEVICE, LIQUID CHROMATOGRAPH, AND METHOD FOR OPERATION OF LIQUID DELIVERY DEVICE

(75) Inventors: Hironori Kaji, Hitachinaka (JP); Hiroyuki Wada, Hitachinaka (JP); Masato Fukuda, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 225 days.

(21) Appl. No.: 12/191,836

(22) Filed: Aug. 14, 2008

(65) Prior Publication Data

US 2009/0057227 A1    Mar. 5, 2009

(30) Foreign Application Priority Data

Aug. 28, 2007   (JP)   ............... 2007-221372

(51) Int. Cl.
    *B01D 15/08*   (2006.01)
(52) U.S. Cl. ............ 210/198.2; 210/101; 210/656; 417/5; 417/22
(58) Field of Classification Search .......... 210/101, 210/137, 198.2, 656; 417/5, 22; 73/61.56
    See application file for complete search history.

(56) References Cited

U.S. PATENT DOCUMENTS

| 2004/0164013 A1 | 8/2004 | Takao et al. |
| 2005/0061722 A1 | 3/2005 | Takao et al. |
| 2005/0084386 A1 | 4/2005 | Mori et al. |
| 2009/0090173 A1* | 4/2009 | Fukuda et al. ............. 73/61.55 |

FOREIGN PATENT DOCUMENTS

| JP | 01-182579 | 7/1989 |
| JP | 01-232261 | 9/1989 |
| JP | 2001-147222 | 5/2001 |
| JP | 3491948 | 2/2004 |
| JP | 2004-150402 | 5/2004 |
| JP | 2005-090410 | 4/2005 |
| JP | 2005-282517 | 10/2005 |
| JP | 3709409 | 10/2005 |

OTHER PUBLICATIONS

Japanese Office Action issued in Japanese Patent Application No. JP 2007-221372 dated Oct. 6, 2009.

* cited by examiner

*Primary Examiner*—Ernest G Therkorn
(74) *Attorney, Agent, or Firm*—McDermott Will & Emery LLP

(57) ABSTRACT

The present invention provides a liquid delivery device for liquid chromatographs which, by performing liquid delivery at an accurate flow rate with limited pulsation, gives accurate results of analyses. The present invention, with a view to preventing erroneous operation due to errors in measurements at the time of judgment of completion of compression of liquid, establishes the judgment point before the pressure measured by a cylinder pressure detector agrees with the pressure measured by a discharge pressure detector and also calculates the point of completion of compression. Control in this manner prevents pressure fluctuation. It also calculates for control the point of completion of compression from the history of compression performed previously.

6 Claims, 6 Drawing Sheets

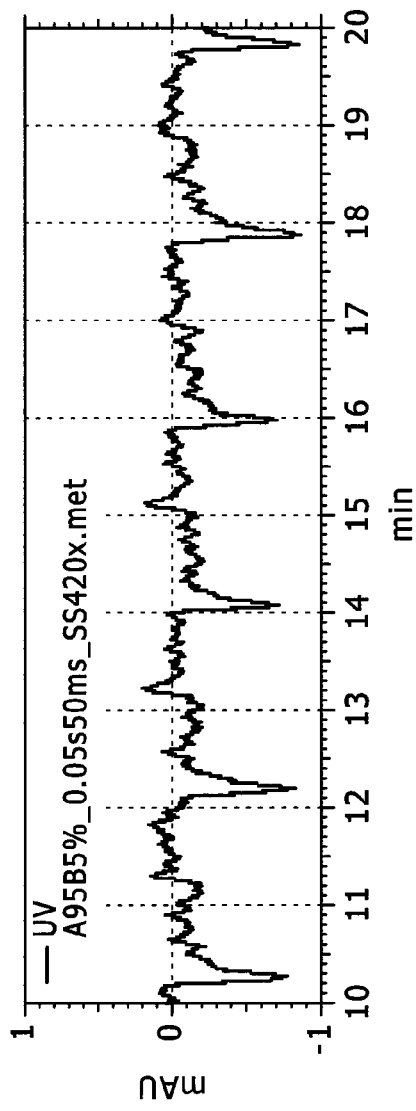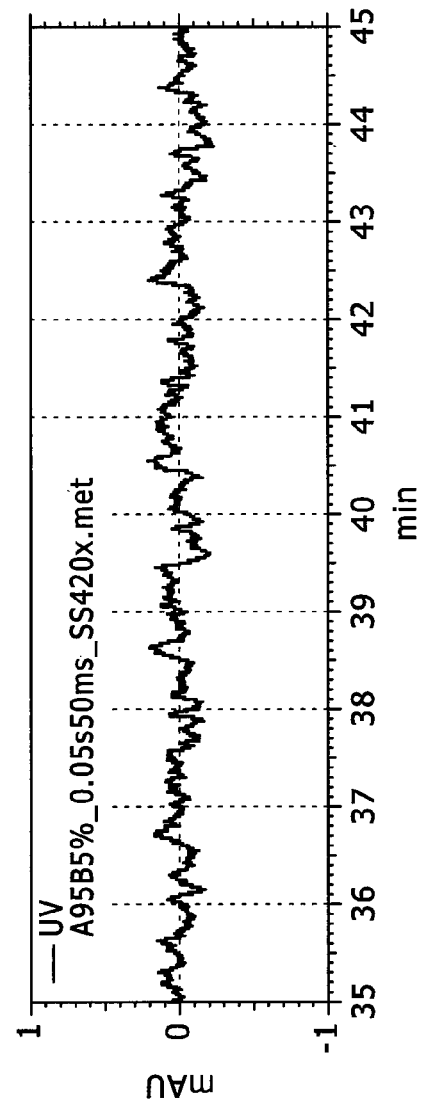

LIQUID DELIVERY DEVICE, LIQUID CHROMATOGRAPH, AND METHOD FOR OPERATION OF LIQUID DELIVERY DEVICE

BACKGROUND OF THE INVENTION

1. Field of the Invention

The present invention relates to a liquid delivery device, a liquid chromatograph, and a method for operation of said liquid delivery device.

2. Description of the Related Art

Any liquid chromatograph is provided with a liquid delivery device, among which is that of reciprocating plunger type. A conventional one of that type usually has two cylinders in each of which a plunger reciprocates, so that it delivers a liquid continuously, with two cylinders repeating sucking and discharging alternately.

Liquid delivery in this manner takes a certain length of time until the cylinder pressure reaches the discharge pressure because the liquid is compressed when the liquid, which has been suck up into the cylinder, is forced out by the plunger. As soon as the liquid is pressurized and the cylinder pressure reaches the discharge pressure, the valve at the discharge side is opened to deliver the liquid.

The drawback of such operation lies in the difficulties of detecting that the cylinder pressure is equal to the discharge pressure and the error of detection that prevents accurate control. This drawback leads to pulsation of liquid delivery that occurs in synchronism with the frequency of plunger movements. Such pulsation causes errors in liquid chromatography as described in Patent Documents 1 and 2.

Patent Document 1: Japanese Patent No. 3491948

Patent Document 2: Japanese Patent No. 3709409

OBJECT AND SUMMARY OF THE INVENTION

The present invention was completed in view of the foregoing. It is an object of the present invention to provide a liquid delivery device, a liquid chromatograph, and a method for operation of said liquid delivery device.

The present invention is directed to an improved liquid delivery device having a plurality of cylinders, each with a reciprocating plunger, a motor to drive said plunger, a control unit to control operation of said motor, a discharge pressure detector to measure the discharge pressure of the eluent being discharged from said cylinders, and a cylinder pressure detector to measure the pressure of said eluent flowing in said cylinders, wherein said improvement is characterized in that said control unit establishes the judgment point before the pressure measured by said cylinder pressure detector agrees with the pressure measured by said discharge pressure detector and controls the speed of rotation of said motor on the basis of the discharge pressure measured by said discharge pressure detector and the pressure measured by said cylinder pressure detector.

The present invention is directed also to an improved liquid delivery device having cylinders arranged in series in more than one stage, plungers reciprocating in said cylinders arranged in more than one stage, a motor to drive said plungers, a control unit to control operation of said motor, a discharge pressure detector to control the discharge pressure of the eluent discharged from the cylinder in the last stage, and a cylinder pressure detector to measure the pressure of said eluent flowing in the cylinder in the initial or middle stage, wherein said improvement is characterized in that said control unit controls the speed of rotation of said motor on the basis of the discharge pressure measured by said discharge pressure detector and the pressure measured by said cylinder pressure detector.

The present invention is directed also to an improved liquid delivery device having a plurality of cylinders, each with a reciprocating plunger, a motor to drive said plunger, a control unit to control operation of said motor, a supply flow channel to supply the eluent from the supply source to said cylinder that functions as a supplier, an inlet check valve attached to said supply channel, an intermediate flow channel to lead said eluent, which has been pressurized in multiple stages including cylinders at said supply side, to said cylinder in the final stage, an outlet check valve attached to said intermediate flow channel, a discharge pressure detector to measure the discharge pressure of said eluent being discharged from said cylinder in the final stage, and a cylinder pressure detector to measure the pressure of said eluent flowing in said cylinders excluding said cylinder in the final stage, wherein said improvement is characterized in that said control unit establishes the judgment point before the pressure measured by the said cylinder pressure detector agrees with the pressure measured by said discharge pressure detector and controls the speed of rotation of said motor on the basis of the discharge pressure measured by said discharge pressure detector and the pressure measured by said cylinder pressure detector.

The present invention is directed also to an improved liquid delivery device having a first cylinder with a first reciprocating plunger and a second cylinder with a second reciprocating plunger, a motor to drive said first and second plungers, a control unit to control operation of said motor, a supply channel to feed an eluent from a supply source to the inlet of said first cylinder, an inlet check valve fitted to said supply channel, an intermediate flow channel to introduce said eluent discharged from the outlet of said first cylinder to the inlet of said second cylinder, an outlet check valve fitted to said intermediate flow channel, a discharge pressure detector to measure the discharge pressure of said eluent being discharged from said second cylinder, and a cylinder pressure detector to measure the pressure of said eluent flowing in said first cylinder, wherein said improvement is characterized in that said control unit establishes the judgment point before the pressure measured by said cylinder pressure detector agrees with the pressure measured by said discharge pressure detector and controls the speed of rotation of said motor on the basis of the discharge pressure measured by said discharge pressure detector and the pressure measured by said cylinder pressure detector.

The present invention is directed also to an improved method for operating a liquid delivery device having a first cylinder with a first reciprocating plunger and a second cylinder with a second reciprocating plunger, a motor to drive said first and second plungers, a control unit to control operation of said motor, a supply channel to feed an eluent from a supply source to the inlet of said first cylinder, an inlet check valve fitted to said supply channel, an intermediate flow channel to introduce said eluent discharged from the outlet of said first cylinder to the inlet of said second cylinder, an outlet check valve fitted to said intermediate flow channel, a discharge pressure detector to measure the discharge pressure of said eluent being discharged from said second cylinder, and a cylinder pressure detector to measure the pressure of said eluent flowing in said first cylinder, with the liquid delivery achieved by one reciprocating cycle of said first and second plungers being divided into three phases, wherein said improvement is characterized in that, in phase 1, said inlet check valve is opened and said outlet check valve is closed so that said eluent is sucked up by said first plunger and said eluent is discharged by said second plunger, phase 2 has the first half section for compression and the second half section for liquid delivery, in said compression section, said inlet check valve and said outlet check valve are closed and said eluent which has been sucked up into said first cylinder is compressed, during which said eluent is discharged by said second plunger, said eluent in said first cylinder is compressed by said first plunger 1, as soon as the pressure (the pressure measured by said cylinder pressure detector) due to this compression reaches the discharge pressure (the pressure measured by said discharge pressure detector) of said second cylinder, said outlet check valve 10 is opened and said compression section shifts to said liquid delivery section, in said liquid delivery section, said first plunger and said second plunger together force out said eluent, in phase 3, said inlet check valve is closed and said outlet check valve is opened, said second plunger sucks up said eluent, said first plunger 1 discharges said eluent, this discharge is combined with the amount which is sucked up by said second plunger, and said motor is controlled in such a way that it runs fast in the compression section of phase 2 and it runs slow in the liquid delivery section of phase 2.

The present invention covers a liquid delivery device capable of delivering an eluent with a minimum fluctuation of pressure, a liquid chromatograph equipped with said liquid delivery device, and a method for operation of said liquid delivery device.

BRIEF DESCRIPTION OF THE DRAWINGS

FIG. 5 is a diagram demonstrating the effect produced by Example 1 of the present invention.

DESCRIPTION OF THE PREFERRED EMBODIMENTS

The examples of the present invention will be described below with reference to the accompanying drawings.

Example 1

The liquid chromatograph equipped with the liquid delivery device will be outlined below with reference to FIG. 1.

Figure 1:
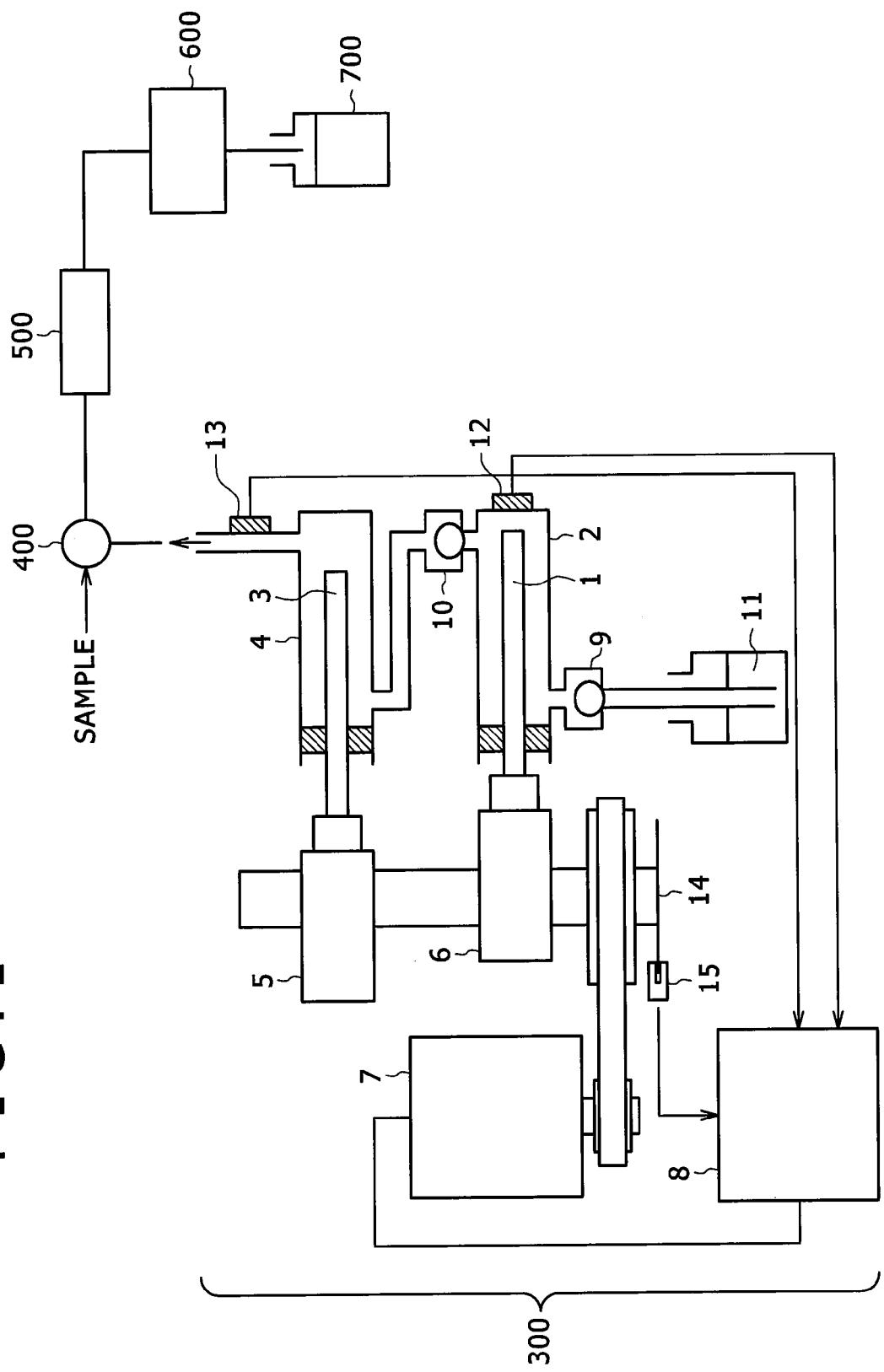
FIG. 1 is a schematic diagram showing a liquid chromatograph with the liquid delivery device according to Example 1 of the present invention.

The liquid chromatograph shown in FIG. 1 consists of a liquid delivery device 300, a sample injector 400, a column 500, a detector 600, and a waste storage 700.

The liquid delivery device 300 has a first cylinder 2 holding therein a first plunger 1 and a second cylinder 4 holding therein a second plunger 3. The plungers are made to reciprocate respectively by a first cam 5 and a second cam 6.

These cams are driven by a motor 7, which is under control by a control unit 8. The first cylinder 2 has an inlet and an outlet which are provided respectively with an inlet check valve 9 and an outlet check valve 10. Thus, it sucks up an eluent 11 through the sucking side of the inlet check valve.

The first cylinder 2 has a cylinder pressure detector 12 to measure the pressure therein, and the second cylinder 4 has a discharge pressure detector 13 to measure the pressure of liquid being discharged. The rotational shaft has a disk 14 attached thereto, which has slits to facilitate detection of cam position by the cam position detecting sensor 15.

A term "supply channel" is used herein to denote the channel through which the eluent 11 is supplied from the eluent reservoir to the inlet of the first cylinder 2. The supply channel is provided with the inlet check valve 9. A term "intermediate channel" is used herein to denote the channel through which the eluent discharged from the outlet of the first cylinder 2 is introduced to the inlet of the second cylinder 4. The intermediate channel is provided with the outlet check valve 10.

Figure 2:
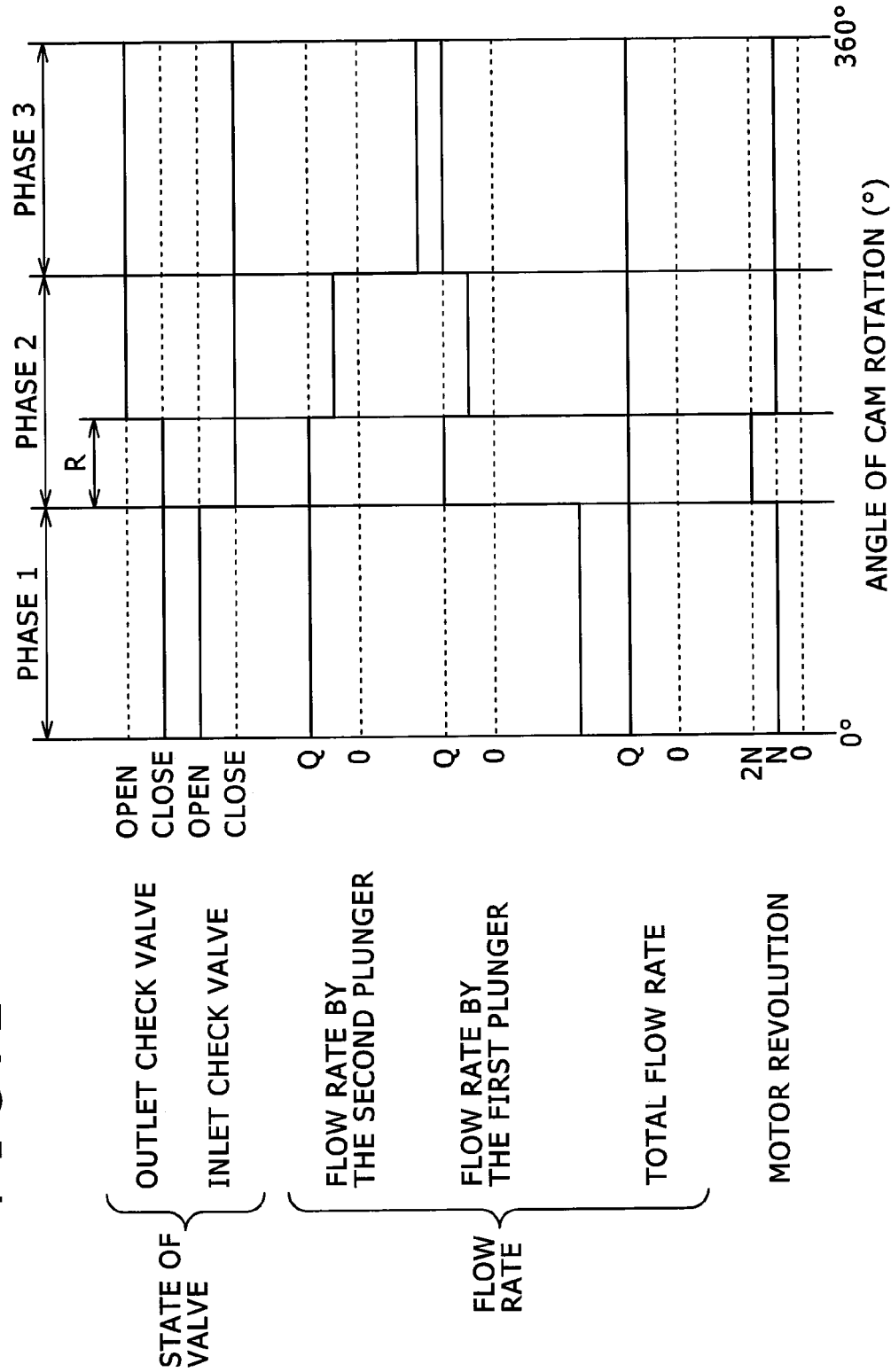
FIG. 2 is a diagram showing how the check valves move and the flow rates change in response to the angle of cam rotation in Example 1 of the present invention.

FIG. 2 shows the movement of each part which corresponds to the rotating angle of the cam.

That is, FIG. 2 shows timing at which the inlet check valve 9 and the outlet check valve 10 open and close within one cycle (or one reciprocating motion of the plunger). It also shows the amount of eluent to be sucked up and discharged by the first plunger 1 and the second plunger 3 and the total amount of liquid delivered by the liquid delivery device in one cycle. It also shows the speed of motor rotation in terms of the angle of cam rotation.

The delivery of the eluent in one cycle is divided into three phases. In phase 1, the first plunger 1 sucks up the eluent 11, with the check valve 9 remaining open and the check valve 10 remaining closed. Also, in phase 1, the second plunger 3 only works to deliver the eluent at a constant flow rate Q.

Phase 2 is further divided into two sections—the first one for compression and the second one for liquid delivery. In the first section of phase 2, the inlet check valve 9 and the outlet check valve 10 are closed, so that the eluent 11 sucked up into the first cylinder 3 is compressed. In this period, only the second plunger 3 discharges the eluent at a prescribed flow rate.

The eluent in the first cylinder is compressed by the first plunger 1 until the pressure in the cylinder reaches the discharge pressure. At a desired pressure, the outlet check valve 10 opens and the second section of phase 2 starts for liquid delivery. In the section for liquid delivery, the eluent is forced out by the first plunger 1 and the second plunger 2.

In phase 3, the inlet check valve 9 remains closed and the outlet check valve 10 remains open. The second plunger 3 moves in such a direction as to suck up the eluent. The first plunger 1 discharges the eluent such that the amount of discharge is the sum of the prescribed amount of pump delivery Q and the amount sucked up by the second plunger.

The compression section R in phase 2 is varied in length according to the discharging pressure of the liquid delivery device. Thus, the liquid delivery device discharges the compressible eluent at a constant flow rate. The compression section R is extended or shortened in proportion to the pressure of the liquid being delivered.

There is a relation as explained below between the compression section R and the flow rate Q (which is the amount of the eluent that is delivered in a unit time). In the compression section R, the outlet check valve 10 is closed, only the second plunger 3 delivers the eluent at a flow rate Q, and the first plunger 1 compresses the eluent which has been sucked up. In this way it is possible to deliver the compressible liquid at a constant flow rate regardless of its degree of compression. This technique is disclosed in Japanese Patent No. 3709409.

According to the disclosed technique, each cam is so curved as to deliver the eluent at Q/2 (or half the prescribed flow rate Q) and the motor 10 is run at twice the normal speed N in the compression section. In this process, the second plunger 3 delivers the eluent at a flow rate Q and the first plunger 1 compresses the eluent. As soon as the compression section R is completed, the rotational speed of the motor 7 returns from 2N to N (normal speed).

In the liquid delivery section of phase 2 and also in phase 3, the outlet check valve 10 remains open. Therefore, in these periods, the first cylinder 2 and the second cylinder 4 have the same pressure. While this state exists, the first pressure detector 12 and the second pressure detector 13 are checked for their calibration.

Problems with this liquid delivery device are errors produced by the two pressure detectors.

Errors are unavoidable in any pressure detectors. They arise from noise in signals, fluctuation due to change in environment (such as ambient temperature), and change with time. They also vary depending on the type of eluent.

For example, if the value indicated by the cylinder pressure detector is lower than the actual one (in which case the pressure in the first cylinder 2 has reached the discharge pressure of the second cylinder 4), the system judges that further compression is necessary and causes the motor to run at twice the normal speed.

In this state, the outlet check valve remains open and both the pressure detectors receive the same pressure. However, the cylinder pressure detector 12 always reads a smaller value than the outlet pressure detector 13, which results in the motor continuing to run at twice the normal speed.

One way of avoiding this trouble in the conventional system was by returning the rotational speed of the motor 7 to normal speed N assuming that the two pressures have reached the same value before the difference between the reading of the outlet pressure detector and the reading of the cylinder pressure detector 12 actually becomes zero. Changing the motor speed in this manner decreases pressure and causes pulsation.

According to the present invention, the foregoing problem is addressed by establishing a point of judgment before the reading of the cylinder pressure detector agrees with the reading of the discharge pressure detector (which is lower than the reading of the discharge pressure detector), thereby calculating the point at which compression is completed. Controlling in this way prevents pressure fluctuation. The history of compression helps calculate the point of completion of compression which permits adequate control.

Figure 3:
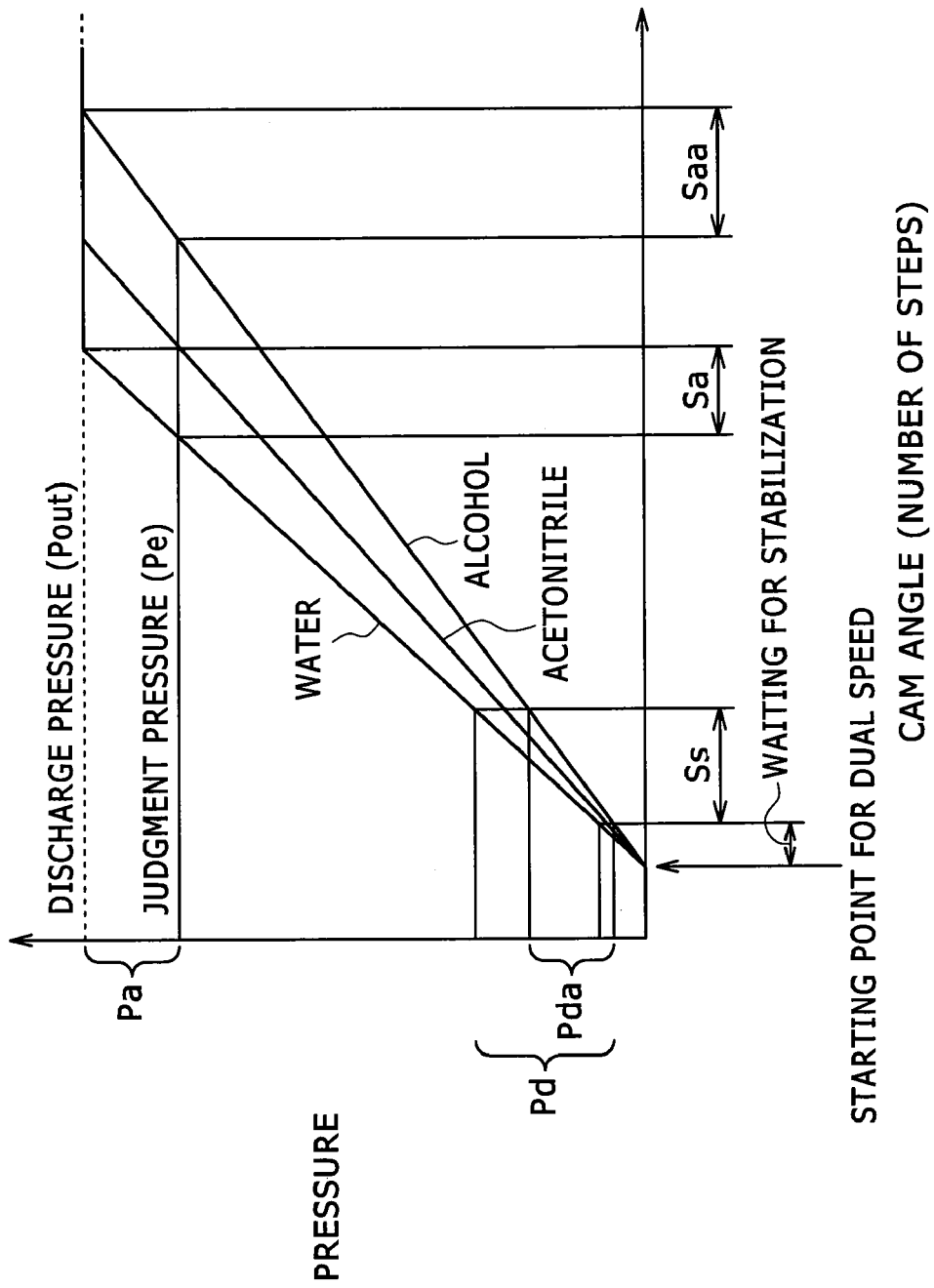
FIG. 3 is a diagram showing the pressure change in the first cylinder that occurs in the compression section in Example 1 of the present invention.

FIG. 3 is a graph showing the change in pressure that occurs in the first cylinder during compression.

In this graph, the abscissa represents the angle of rotation of the cam and the ordinate represents the change of pressure in the first cylinder. As soon as the sucking of the eluent is complete, the compression cycle starts. The starting point of the compression cycle is determined as the cam position detector 15 senses the cam angle. As mentioned above, the motor 12 runs twice the normal speed in the compression cycle.

First, the rate of change in pressure (denoted by K) is obtained after a certain length of period required for the system to stabilize, which is measured from the point at which the motor starts to run at twice the normal speed in the compression cycle. The value of K, which represents the slope of pressure increase in the first cylinder 2, is calculated from the pressure increase (Pd) corresponding to the predetermined step value (Ss) which is measured by the cylinder pressure detector 12. Incidentally, the motor 7 is a step motor whose angle of rotation depends on the number of pulses.

Next, the extended period (or step value), denoted by Sa, is obtained from Sa=Ss/Pd·Pa. Then, compression is continued, with the motor running at twice the normal speed, until the judgment pressure (Pe=Pout−Pa) holds. Additional compression in this manner is carried out for a period corresponding to Sa. After that, the delivery of eluent is continued, with the motor running at the predetermined normal speed.

The number of steps (Sa), which corresponds to the extended period, equals that for Pa (the width of values established for pressure).

As soon as the judgment pressure (Pe) is reached, the motor is run for the number of steps (Sa), which corresponds to Pa (the width of values established for pressure) previously obtained from K (the rate of change in pressure), and the compression section R in phase 2 (with the motor running twice the normal speed) terminates. Operation in this manner eliminates pulsation which results from the motor running at twice the normal speed and the pressure decreasing in the conventional technology.

FIG. 3 shows the behavior of water, alcohol, and acetonitrile as the eluent. They vary in K (the rate of change in pressure) according as they vary in compressibility. This problem is addressed by operation in the foregoing manner which terminates the compression section R (with the motor running twice the normal speed) which is calculated from K (the rate of change in pressure) for individual species of eluent. In this way it is possible to eliminate pulsation which results from the motor running at twice the normal speed and the pressure decreasing.

Incidentally, the motor 7 is a step motor as mentioned above. The high speed rotation (at twice the normal speed) and the low speed rotation are controlled by the cam position detecting sensor 15. Control in this manner is accomplished accurately because the step motor turns through any angle in response to the number of pulses. Therefore, the step motor permits accurately controlled rotation.

The motor 7 is controlled by the program stored in the control unit 8.

Figure 6:
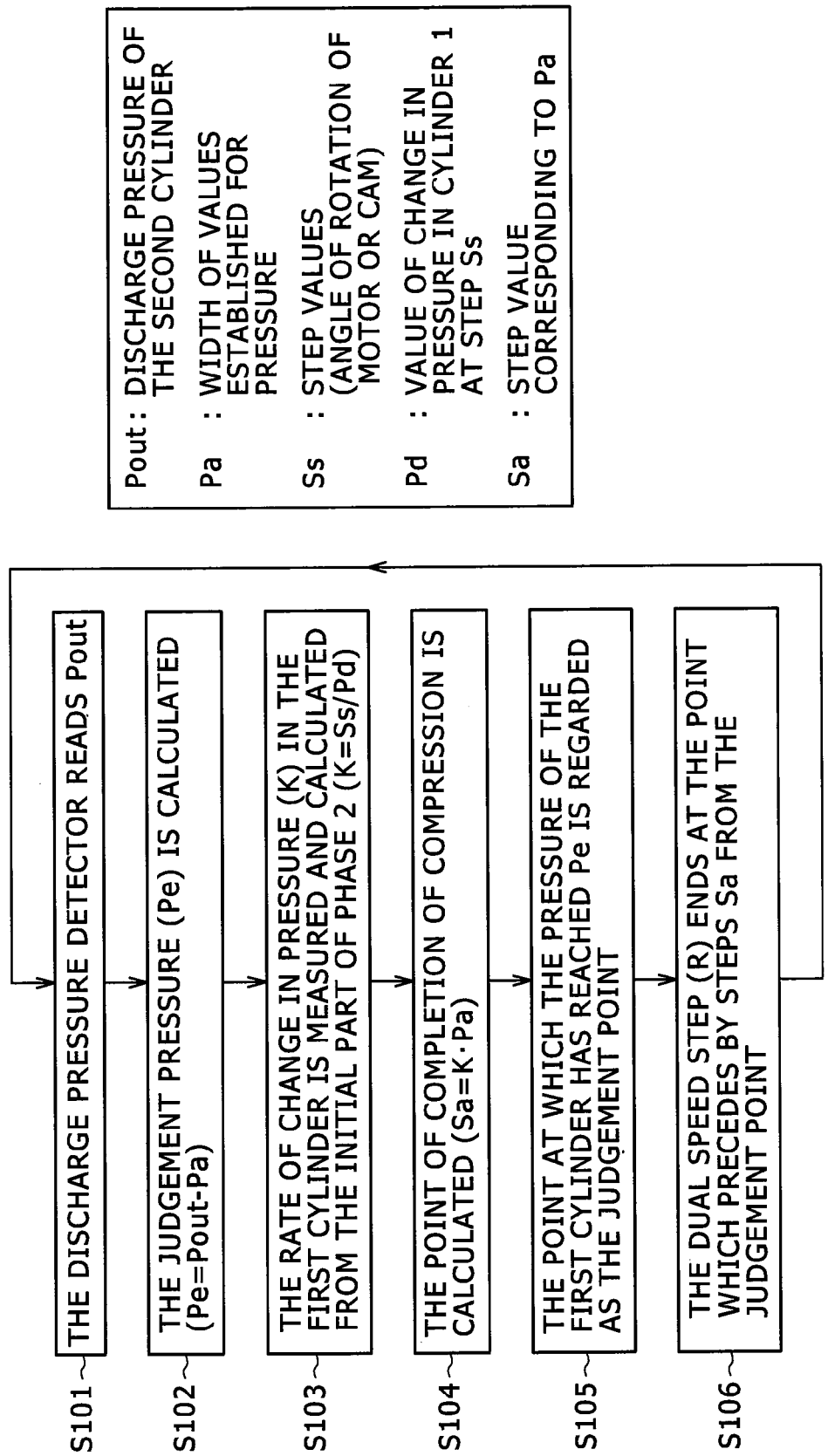
FIG. 6 is a flow sheet showing the steps from the start of operation in compression section R (with the motor running at twice the normal speed) to the end of operation.

FIG. 6 is a flow chart showing steps from the start of the compression section R (with the motor running at twice the normal speed) to the end of operation.

In Step S101, the discharge pressure detector reads the discharge pressure (Pout) of the second cylinder. In Step S102, the judgment pressure (Pe) is calculated from Pe=Pout−Pa (where Pa is the width of pressure values which may be established arbitrarily).

The judgment pressure (Pe) is lower than the discharge pressure (Pout), and it occurs before compression is completed in the compression section (R) of phase 2.

In Step S103, the rate of change in pressure (K) in the first cylinder is measured and calculated from the initial part of phase 2 (K=Ss/Pd). K varies depending of the species, temperature, and aging of the eluent. The pressure of the first cylinder should be measured after it has become stable, so that the rate of change in pressure (K) can be measured more adequately.

In Step S104, the point of completion of compression is calculated (Sa=K·Pa). In Step S105, the system confirms that the pressure of the first cylinder has reached the judgment pressure. In Step S106, the motor continues to rotate for a period equivalent to the extended section (Sa minutes) from the judgment point, and the compression section R (for the motor running twice the normal speed) terminates. The foregoing steps are repeated.

The steps starting from the compression section R to the termination of operation are implemented according to programs stored in memory in the control unit 8.

Example 2

Figure 4:
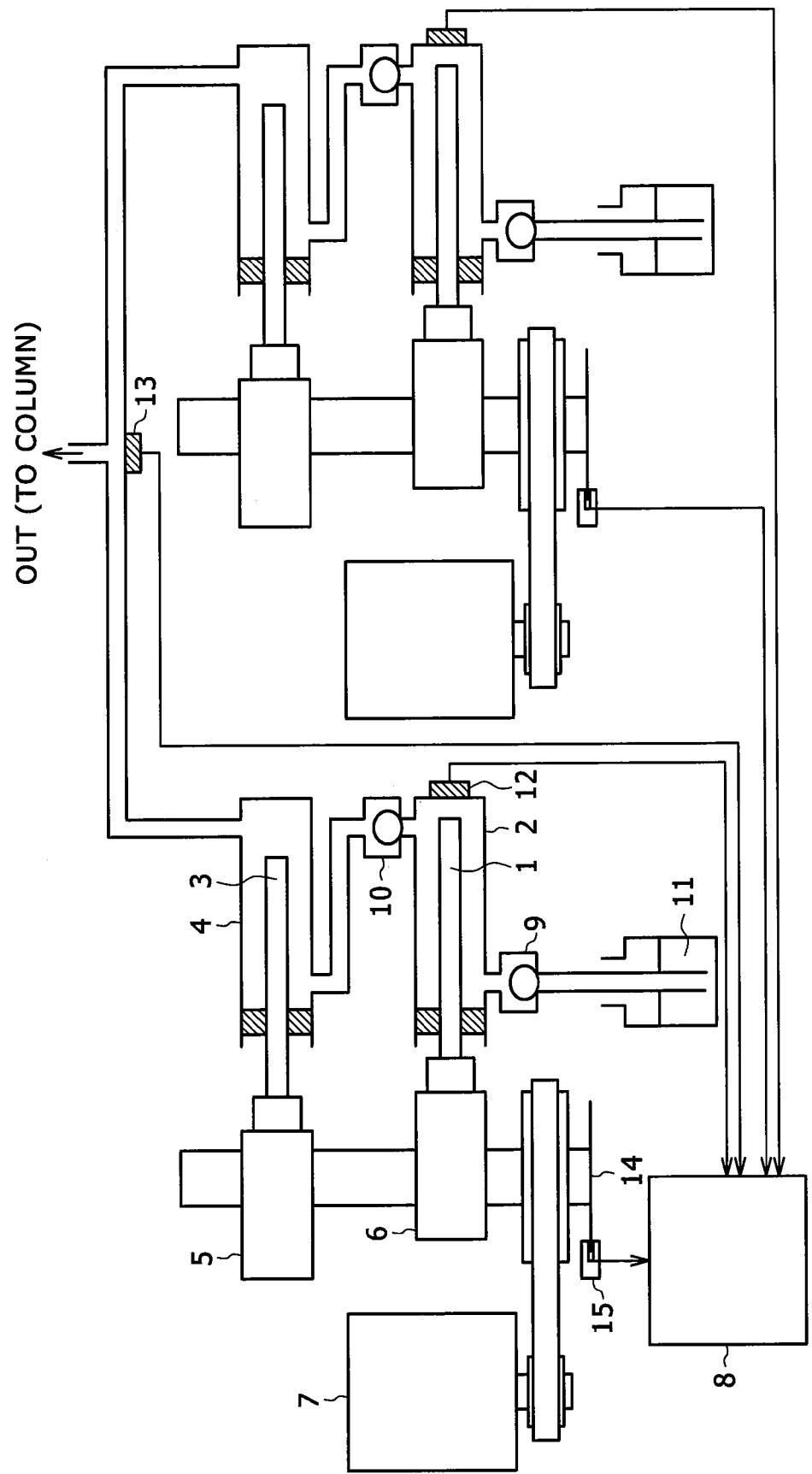
FIG. 4 a schematic diagram showing the liquid delivery device according to Example 2 of the present invention.

FIG. 4 shows another example of the present invention.

This example demonstrates the so-called "high-pressure gradient" system, which is so designed as to deliver a mixture of solvents whose mixing ratio varies gradually. The gradient system according to this example is comprised of two units of the liquid delivery device described in Example 1. It has one pressure detector to measure the discharge pressure and control two pumps.

An ordinary high-pressure gradient system hardly produces a stable flow rate on account of two pumps interfering with each other. This interference occurs when the pressure detector to control the flow rate of one pump is affected by pressure fluctuation arising from the action of the other pump, and it disturbs control. This is not the case with the present invention in which the read value of discharge pressure is not used for control and hence no interference occurs. Thus the high-pressure gradient system according to the present invention is able to deliver a mixture of solvents in a stable mixing ratio at a stable flow rate.

FIGS. 5(a) and 5(b) show respectively the effect produced without or with control according to the present invention. The former suffers periodic pressure decrease, whereas the latter is free of periodic disturbance.

What is claimed is:

1. An improved liquid delivery device having cylinders arranged in series in more than one stage, plungers reciprocating in said cylinders arranged in more than one stage, a motor to drive said plungers, a control unit to control operation of said motor, a discharge pressure detector to control the discharge pressure of the liquid discharged from the cylinder in the last stage, and a cylinder pressure detector to measure the pressure of said liquid flowing in the cylinder in the initial or middle stage, wherein said improvement is characterized in that said control unit establishes the judgment point before the pressure measured by said cylinder pressure detector agrees with the pressure measured by said discharge pressure detector and controls the speed of rotation of said motor on the basis of the discharge pressure measured by said discharge pressure detector and the pressure measured by said cylinder pressure detector.

2. An improved liquid delivery device having a first cylinder with a first reciprocating plunger and a second cylinder with a second reciprocating plunger, a motor to drive said first and second plungers, a control unit to control operation of said motor, a supply channel to feed an eluent from a supply source to the inlet of said first cylinder, an inlet valve means fitted to said supply channel, an intermediate flow channel to introduce said eluent discharged from the outlet of said first cylinder to the inlet of said second cylinder, an outlet valve means fitted to said intermediate flow channel, a discharge pressure detector to measure the discharge pressure of said eluent being discharged from said second cylinder, and a cylinder pressure detector to measure the pressure of said eluent flowing in said first cylinder, wherein said improvement is characterized in that said control unit establishes the judgment point before the pressure measured by said cylinder pressure detector agrees with the pressure measured by said discharge pressure detector and controls the speed of rotation of said motor on the basis of the discharge pressure measured by said discharge pressure detector and the pressure measured by said cylinder pressure detector.

3. An improved liquid delivery device having a first cylinder with a first reciprocating plunger and a second cylinder with a second reciprocating plunger, a motor to drive said first and second plungers, a control unit to control operation of said motor, a supply channel to feed a liquid from a supply source to the inlet of said first cylinder, an inlet check valve fitted to said supply channel, an intermediate flow channel to introduce said liquid discharged from the outlet of said first cylinder to the inlet of said second cylinder, an outlet check valve fitted to said intermediate flow channel, a discharge pressure detector to measure the discharge pressure of said liquid being discharged from said second cylinder, and a cylinder pressure detector to measure the pressure of said liquid flowing in said first cylinder, wherein said improvement is characterized in that said control unit establishes the judgment point before the pressure measured by said cylinder pressure detector agrees with the pressure measured by said discharge pressure detector and controls the speed of rotation of said motor on the basis of the discharge pressure measured by said discharge pressure detector and the pressure measured by said cylinder pressure detector.

4. The liquid delivery device as defined in claim 3, wherein said control unit has a control function to change the speed of rotation of said motor when the pressure measured by said cylinder pressure detector reaches the discharge pressure measured by said discharge pressure detector during the pressuring motion in which said first cylinder pressurizes said liquid.

5. The liquid delivery device as defined in claim 3, wherein said control unit has a control function to lower the speed of rotation of said motor when the pressure measured by said cylinder pressure detector reaches the discharge pressure measured by said discharge pressure detector during the pressuring motion in which said first cylinder pressurizes said liquid.

6. The liquid delivery device as defined in claim 3, wherein the values measured by said discharge pressure detector and said cylinder pressure detector are calibrated on the basis of the values which are measured by said discharge pressure detector and said cylinder pressure detector while said outlet check value is open.

* * * * *